United States Patent [19]

Ruell et al.

[11] 4,428,670

[45] Jan. 31, 1984

[54] FINGERPRINT SENSING DEVICE FOR DERIVING AN ELECTRIC SIGNAL

[75] Inventors: Hartwig Ruell, Mount Laurel; Edward J. Devinney, Jr., Delanco; Ming-Yee Chiu, Voorhees, all of N.J.

[73] Assignee: Siemens Corporation, Iselin, N.J.

[21] Appl. No.: 317,401

[22] Filed: Nov. 2, 1981

Related U.S. Application Data

[63] Continuation of Ser. No. 176,701, Aug. 11, 1980, abandoned.

[51] Int. Cl.³ .................... G06K 9/00; G01N 21/17
[52] U.S. Cl. ..................................... 356/71; 356/445
[58] Field of Search ................ 356/71, 371, 394, 445, 356/446, 448, 239, 352, 447; 340/146.3 E, 146.3 F, 146.3 G; 250/566; 350/162 SF, 162 ZP, 266, 276

[56] References Cited

U.S. PATENT DOCUMENTS

| | | | |
|---|---|---|---|
| 3,138,059 | 6/1964 | White | 356/389 |
| 3,478,218 | 11/1969 | Wuellner et al. | 356/239 |
| 3,815,998 | 6/1974 | Tietze | 356/371 |
| 3,975,711 | 8/1976 | McMahon | 356/71 |
| 4,322,163 | 3/1982 | Schiller | 356/71 |

OTHER PUBLICATIONS

Budde, W., "A Reference Instrument For 20°, 60° & 85° Gloss Measurements" Metrologia, Springer-Verlag, 2/80, pp. 1–5.

Primary Examiner—William H. Punter
Attorney, Agent, or Firm—Karl F. Milde, Jr.

[57] ABSTRACT

The fingerprint sensor derives an electric output signal in accordance with the topographic relief of the finger under investigation. The sensor incorporates a contact body which is formed at least in part by a light-transparent elastic material. The contact body, preferably a flat sensor plate made of said elastic material and attached to a flat supporting plate, has a light receiving surface and a contact surface for receiving a contact pressure by the finger. Before an investigation process is started, the contact surface is smooth. By pressing the finger against the contact surface, the contact surface will attain a shape conforming to the fingerprint pattern of the finger. The sensor also incorporates a light source, a photodetector and an optical system. The light source obliquely passes light to the contact surface which reflects a light beam modulated in accordance with the fingerprint. The optical system passes the reflected light beam to the light sensitive area of the photodetector. In the optical path between finger and photodetector is included a light stop for blocking reflected light which does not contain fingerprint information.

17 Claims, 5 Drawing Figures

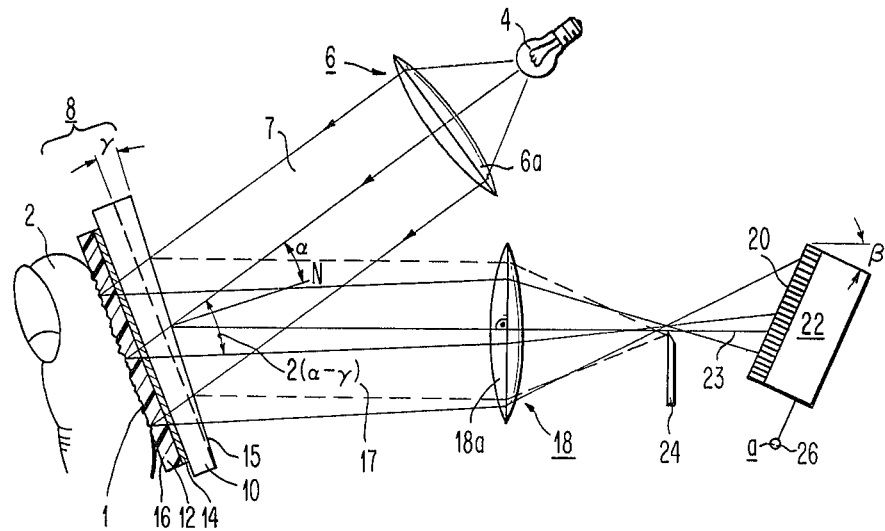
FIG. 1
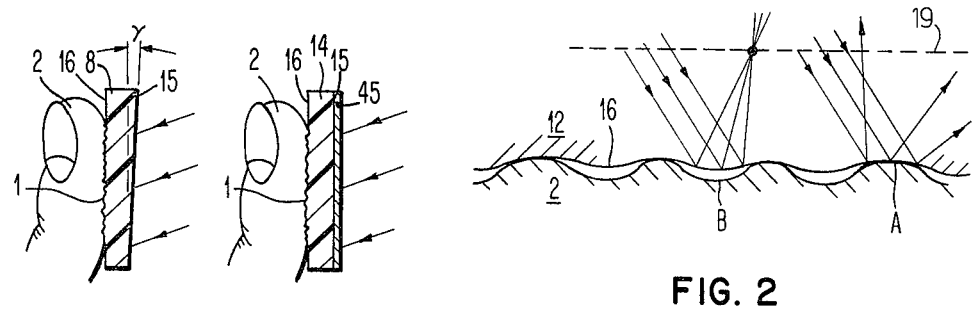
FIG. 3    FIG. 5
FIG. 2
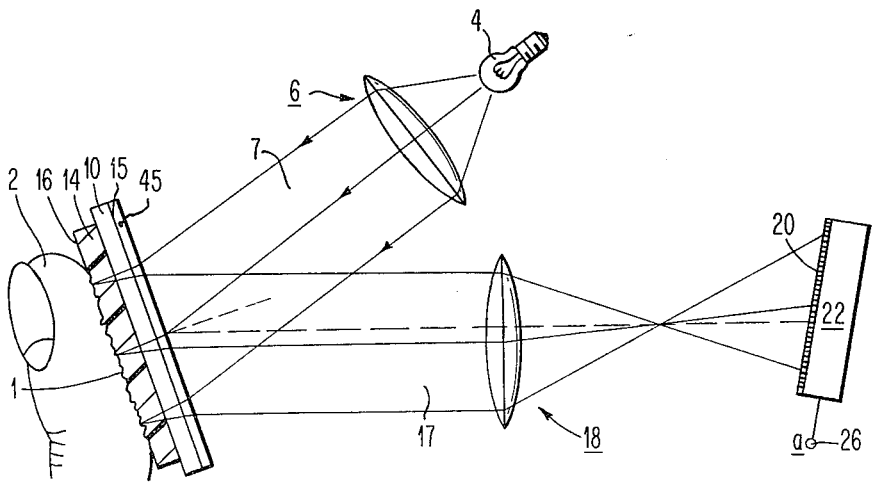
FIG. 4

FINGERPRINT SENSING DEVICE FOR DERIVING AN ELECTRIC SIGNAL

This application is a continuation of application Ser. No. 176,701, filed Aug. 11, 1980 and now abandoned.

CROSS REFERENCE TO RELATED APPLICATIONS

This application relates to the same technical field as the commonly owned applications of Hartwig Ruell, Edward J. Divinney and Ming-Yee Chiu, entitled "Fingerprint Sensor for Deriving an Electric Signal", Ser. No. 176,695 and "Fingerprint Sensor Assembly for Deriving an Electric Output Signal", Ser. No. 176,699, both filed on Aug. 11, 1980 and now abandoned.

BACKGROUND OF THE INVENTION

1. Field of the Invention

This invention relates in general to a device for identifying an individual by identification of his/her fingerprint. In particular, this invention relates to a fingerprint sensor for transforming the information contained in a person's fingerprint into an electric output signal. Still more particularly, this invention relates to a fingerprint sensor using optical means for reading a fingerprint.

2. Description of the Prior Art

Fingerprint identification systems which identify the print of a finger pressed on a contact surface are well-known in the art.

U.S. Pat. No. 4,053,228, for instance, discloses a finger identification apparatus which contains a transparent glass plate serving as a contact surface or fingerprint reader. A fingerprint is formed by pressing the finger under investigation against the back surface of the glass plate and holding it in a predetermined position thereon. The fingerprint is interrogated by a light beam directed through the front surface of the glass plate. The interrogating beam is partially reflected at the back surface to provide a signal beam which carries the fingerprint information. The reflected signal beam is then correlated against a hologram of the same fingerprint in order to provide the identification of the individual.

In U.S. Pat. No. 4,120,585, another fingerprint identification system is disclosed. This system contains a pliable optical prism as a fingerprint sensor. The base of the prism is physically contacted by the finger of the person under investigation. The pliable prism deforms under the applied pressure. It partially reflects a sensing light beam to a photo-sensitive device which will be activated. The photo-sensitive device, in turn, activates further optical components of the fingerprint identification system. A fingerprint reader is examined for the ridge-valley pattern of the fingerprint of a person to be identified. It should be mentioned that in this prior art system the prism surface is deformed or bent as a whole. The finger does not impress a pattern into the surface in order to obtain therein the configuration of the topographical relief of the finger.

The prior fingerprint identification systems require highly sophisticated technology. Yet, a fingerprint identification system should easily and inexpensively be assembled, and simultaneously it should afford a high image quality of the fingerprints. Particularly, the fingerprint image should be free from distortions.

SUMMARY OF THE INVENTION

1. Objects

It is an object of the invention to provide a fingerprint sensor for transforming the fingerprint information of a contacting finger into a readable optical image and therefrom into an electric output signal.

It is another object of this invention to provide a fingerprint sensor the electric output signal of which represents the information contained in the fingerprint and can be read into a computer for further processing.

It is still another object of this invention to provide a fingerprint sensor which is easy to assemble, requires low cost, provides high sensitivity and resolution, and affords a high reliability.

It is still another object of this invention to design a fingerprint sensor which provides fingerprint images of high quality that are to a large extent free from distortions.

It is still another object of this invention to provide a fingerprint sensor which applies Schlieren techniques in order to improve the contrast of the fingerprint images.

It is still another object of this invention to provide a fingerprint sensor the output signal of which allows for digital processing of fingerprint images.

It is still another object of this invention to provide a fingerprint sensor which avoids laser scanning techniques.

2. Summary

According to this invention, a fingerprint sensor for transforming the fingerprint information of a contacting finger into an electric output signal incorporates a contact body which is at least in part made of a light-transparent and elastic or resilient material. This contact body contains a light receiving surface for receiving light and a contact surface for receiving a contact pressure from the finger under investigation. The contact surface is formed by the elastic material. It is smooth before a finger investigation is started. Yet, when the finger is pressed against the contact surface, the smooth structure of the surface will be changed in accordance with the fingerprint pattern, due to the elastic properties of the material chosen. After taking away the finger from the contact surface, the contact surface will resume its former structure, that is, it will become even and smooth again.

The fingerprint sensor further incorporates a light source. The light source directs a primary light beam in forward direction through the light receiving surface to the contact surface. The primary light beam enters the light receiving surface obliquely with respect to the normal of this surface. In the presence of the pressing finger, the contact surface will specularly remit or reflect a light beam in backward direction through the light receiving surface. The reflected light beam is modulated in accordance with the fingerprint pattern of the finger.

The fingerprint sensor further incorporates an optical system and a photodetector. The photodetector has a light sensitive area for measuring the distribution of light which impinges on this area. The optical system transmits the reflected and modulated light from the contact surface to the light sensitive area of the photodetector.

Contained in the optical path between finger and light sensitive area is a light stop which is used for blocking a part of the reflected light. Particularly, this light stop may be a sharp knife-like edge or knife-edge which catches the image of the light source, and which allows the specularly reflected light from the finger to pass to the light sensitive area. The fingerprint sensor finally incorporates an output which is associated with the photodetector for obtaining the electric output signal.

The elastic or resilient material which forms the contact surface of the contact body may be a polymer. Silicone rubber, an elastomer, has been found particularly useful.

In a preferred embodiment, the contact body has a first and a second planar face end. Both face ends are arranged not exactly parallel to each other, but positioned at a small wedge or acute angle with respect to each other. This angle may be smaller than 5°, particularly smaller than 3°. The first of these face ends is the light receiving surface, and the second face end is the contact surface for receiving the contact pressure of the finger. In this embodiment, the contact body may be made entirely or partially of the light-transparent and elastic material. In a preferred version, a support plate may be attached to a sensor plate made of the light-transparent and elastic material. The support plate may be made of glass. It provides a sufficient resistance when a finger is pressed against the contact surface. Since a wedge-shaped contact body is used, light which is reflected from the light receiving surface is shifted sideways with respect to light which is emitted from the fingerprint, especially when light focussing means are used. Therefore, the light reflected from the light receiving surface, which does not contain any fingerprint information, may be blocked by a knife-edge or by a similar light stop.

The foregoing and other objects, features and advantages of the invention will be apparent from the following more particular description of preferred embodiments of the invention, as illustrated in the accompanying drawings.

BRIEF DESCRIPTION OF THE DRAWINGS

In the drawings:

FIG. 1 is a fingerprint sensor incorporating a contact plate and a wedge-shaped support plate, according to the invention;

FIG. 2 is a cross section of the interface finger/contact plate;

FIG. 3 is a wedge-shaped contact plate, which is touched by a finger under investigation;

FIG. 4 is a fingerprint sensor incorporating a contact plate and a support plate coated with an antireflection medium; and FIG. 5 is a contact plate which is coated with an antireflection medium, the plate being touched by a finger under investigation.

DETAILED DESCRIPTION OF THE PREFERRED EMBODIMENT

With reference to FIG. 1, a fingerprint sensor for deriving an electric output signal a in accordance with the topographic relief, pattern or print 1 of a finger 2 under investigation is illustrated.

The fingerprint sensor incorporates a light source 4 which emits a light beam for sensing the fingerprint 1. The light source 4 may be a light source which emits white light, for instance, such as a regular light bulb. As illustrated, in the present embodiment the light source 4 is a small incandescent light source. The light source 4 may also be a light emitting diode (LED) or a semi-conductor laser which emits light of a specific wavelength. The wavelength of the light may be located in the infrared spectrum. However, it is considered one of the advantages of the present invention that a light source 4 can be applied which emits a wide spectrum of light.

The light of the light source 4 is collected by a first optical system 6 which contains a collimator lens 6a. The optical system 6 directs a parallel light beam 7 towards a light-transparent contact body 8. If a small light source 4 is used, which is located far away, the first optical system 6 may be omitted.

In FIG. 1, the contact body 8 is designed as a wedge-shaped plate assembly. It consists of a support plate 10 having two end faces which are arranged as to have a small acute or wedge angle $\gamma$ inbetween, and a flat contact or sensor plate 12, having parallel end faces. The term "small acute angle" as used herein means an angle of less than 20°. The angle $\gamma$ should be less than 5°. Depending on the geometry, it may be less than 3°. Between the two plates 10 and 12 is arranged an optically matching medium 14. The matching medium 14 is a substance which matches the index of refraction of the support plate 10 to the index of refraction of the adjacent contact plate 12.

As mentioned above, the contact 8 contains a wedge-shaped support plate 10 and a flat sensor plate 12. The support plate 10 has an inner and an outer planar end face. The outer or right end face is a light receiving surface 15. The normal of the light receiving surface is designated as N.

The sensor plate 12 is made of a light-transparent elastic material. This elastic material may be an elastomer such as a polymer. Preferably, the material of the sensor plate 12 may be a silicone rubber. The sensor plate 12 has an inner and an outer planar end face. Both end faces are arranged parallel to each other. The outer or left end face is a contact surface 16 for exercising a contact pressure thereon by means of the finger 2. When the finger 2 does not touch the sensor plate 12, the contact surface 16 will be smooth and even. Yet, when the finger 2 is pressed against the contact surface 16, the structure of the contact surface 16 will change. The contact surface 16 will now obtain a pattern which is in accordance with the topographic relief of the crests and valleys of the fingerprint.

The support plate 10 provides rigidity and strength to the plate assembly 8 which is needed when the finger 2 is pressed against the contact surface 16. The support plate 10 may be made of a light-transparent plastic. Preferably it may be made of glass. Preferably a material may be chosen the index of refraction of which is approximately equal to the index of refraction of the elastic material.

The light beam 7 from the light source 4 hits the light receiving surface 15 obliquely. The angle of incidence with respect to the normal is designated as $\alpha$. The light beam 7 passes through the light receiving surface 15 and enters the support plate 10. Then it passes through the matching medium 14. Subsequently, it enters the sensor plate 12, and finally it hits the outer surface or contact surface 16 of the sensor plate 12. When the contact surface 16 is contacted by the skin of the finger 2, a partially specular reflection takes place.

The light beam 17 reflected from the contact body 8 is shown partially in solid lines and partially in broken lines. One portion (broken lines) of the light beam 17 is reflected from the light receiving surface 15. This portion does not contain any fingerprint information. Another portion (solid lines) is reflected from the fingerprint 1. This portion is spatially modulated by the topological structure of the finger 2. The reflected light beam 17 in total, therefore, carries the information about the fingerprint. It is reflected towards the right side of the fingerprint sensor, that is, the same side where the light source 4 is located.

Subsequently, the light beam 17 passes through a second optical system 18. As illustrated, the second optical system 18 may contain the lens 18a or the lens system of a large aperture camera.

Finally, the reflected light beam 17 partially hits the light sensitive area 20 of a photodetector 22. The photodetector 22 is provided for measuring the distribution of light impinging on its light sensitive area 20. The light sensitive area 22 may be made up of an array of individual photo-sensitive elements. The output signals of these elements are fed into a digital image processing device which is incorporated into the photodetector 22. From the output 26 of the photodetector 22 the electrical output signal a is derived.

With respect to the imaging lens 18a of the second optical system 18 the photodetector 22 is positioned such that the image of the fingerprint 1 is sharply focussed on the light sensitive area 20. To this end, the photodetector 22 is tilted by an angle $\beta$ about an axis which is perpendicular to the optical axis 23 of the second optical system 18. A light blocking device or light stop 24, which may be a sharp knife-like edge, a razor blade, or a small disc, is positioned between the imaging lens 18a and the light sensitive area 20 in order to obtain a fingerprint image having a good contrast. The light stop 24 is positioned such that its tip blocks partially the reflected light beam 17. Particularly, it is positioned such that it catches the image of the incandescent light source 4. Still more particularly, it is positioned such that it prevents the portion of light (broken lines) directly reflected from the light receiving surface 15 from passing on to the light sensitive area 20. If a first optical system 6 is applied which provides for a parallel beam 7, the tip of the light stop 24 should be arranged in the focal plane of the imaging lens 18, where the directly reflected light is focussed. To date, knife edges or other spatial filters have already been used in so-called Schlieren set-ups (see OPTICS by Hecht et al., Addison-Weseley Pub. Corp., Feb. 1979, pp. 478–481).

As mentioned above, a silicone polymer or rubber can be used as the light-transparent transducer material for the sensor plate 12. Silicone oil may be used as the matching medium 14. This oil will establish a good mechanical contact and a good optical interface between the sensor plate 12 and the glass support plate 10. By using silicone oil or another matching medium 14, multiple reflections can be avoided. Instead of a silicone oil, an optical cement with a properly chosen index of refraction can be applied. Also an optical glue with the same properties can be used to bond the elastomer contact plate 12 directly to the glass support plate 10.

In another embodiment (not shown), the sensor material 12, for instance silicone polymer, may be directly coated on the left or outer end face of the support plate 10. In this embodiment, it is not necessary to use an index matching substance 14.

The photodetector 22 may be a standard video camera (vidicon camera). Such a video camera has the advantage that it may interface to a microcomputer. Yet, it is also possible to use a commercially available CCD matrix or a CID matrix of photodetector elements. Such an embodiment may be chosen for the sake of simplicity and reliability. It may also reduce the costs and the size of the fingerprint sensor.

It should be mentioned again that the light source 4 illuminates the light receiving surface 15 from an oblique angle $\alpha$. Therefore, the directly reflected light from the surface 15 (air-glass interface) as well as the specularly reflected light from the fingerprint 1 (elastomer-air interface) is collected by the large aperture camera lens 18a of the second optical system 18. The reflection from the adjacent side ends of the plates 10 and 12 (glass-elastomer interface) is negligible if the indices of refraction are almost the same for both glass and elastomer. The light reflected from the outer or front surface 15 of the support plate 10 (air-glass interface) contains no information about the fingerprint structure and represents a sort of DC background which tends to degrade the contrast of the fingerprint image. In the present embodiment, this DC background is eliminated by using a support plate 10 with a small wedge angle $\gamma$ so that the image of the light source 4 is shifted sideways and is blocked by the light stop 24. The light reflected from the contact surface 16 contains the fingerprint information and forms an image on the light sensitive area 22. The output signal a corresponding to this image can be stored and processed.

As shown in FIG. 2, the contact surface 16 is deformed according to the topology of the skin, when the finger 2 is pressed against the silicone elastomer contact surface 16. At a ridge portion A of the finger 2, the skin is in contact with the contact surface 16 and light is coupled out of the sensor plate 12. The light is partially absorbed and partially scattered by the rough surface of the finger skin. At a valley portion B of the skin, however, the contact surface 16 is a good optical surface, because there is no contact between the contact surface 16 and the rough finger skin. The valley portion B reflects the light specularly. Since the material of the sensor plate 12 is flexible, the contact surface 16 locally forms a small concave focussing mirror. Therefore, a high contrast image can be obtained if the camera lens 18a is focussed on the plane 19 a little distance away from the plane between the finger 2 and the sensor plate 12.

The imaging of the fingerprint 1 may roughly be one to one. Therefore, a distortion which might be due to an oblique viewing of the finger 2 is corrected by tilting the photodetector 22 about a tilting angle $\beta = \alpha + \gamma$, so that photo sensitive area 20 is in the same plane as the image of the fingerprint 1. In this way, the image of the fingerprint 1 is in sharp focus.

In FIG. 3 is illustrated that a wedge-shaped sensor body 8 may be used which is entirely made out of the above-mentioned light-transparent material. Both surfaces 15 and 16 are made of this material.

FIGS. 4 and 5 illustrate that the light reflected from the front surface 15 may also be eliminated by applying an antireflection coating 45 on the front surface of a support plate 10 or a sensor body 8 which is entirely made out of light-transparent material, respectively. In FIGS. 4 and 5, the coating 45 acts as a light stop.

As shown in FIG. 4, the plates 10 and 14 possess parallel end faces. The outer end face 15 of the support plate 10 is coated with a thin film 45 of antireflection material similar to the lens of a photo-camera. As shown in FIG. 5, the thin film 45 may also be applied directly to the outer surface 15 of the contact plate 14 if a support plate 10 is not used.

There has thus been shown and described a novel fingerprint sensor which fulfills all the objects and advantages sought therefore. Many changes, modifications, variations and other uses and applications of the subject invention will, however, become apparent to those skilled in the art after considering this specification and the accompanying drawings which disclose preferred embodiments thereof. All such changes, modifications, variations and other uses and applications which do not depart from the spirit and scope of the invention are deemed to be covered by the invention which is limited only by the claims which follow.

What is claimed is:

1. A fingerprint sensor for deriving an electric output signal according to the ridges and valleys of a finger under investigation, said sensor comprising, in combination:
   (a) an elastic, pressure-sensitive contact surface formed by a transparent elastic material for receiving a contact pressure by said finger, thereby changing the structure of said surface in accordance with the fingerprint pattern of ridges and valleys of said finger, whereby the regions of the contact surface associated with the fingerprint valleys are not in contact with the finger and form small concave focusing mirrors, having their focal points along a focusing plane which is parallel to, and at the focal distance of said focusing mirrors away from, said contact surface;
   (b) a light source for passing substantially parallel light through said transparent elastic material to said contact surface, whereby in the presence of said finger said regions of the contact surface associated with the valleys which form said focusing mirrors reflect the light impinging on these regions and focus this light at said focusing plane, thus forming a focused light pattern at said plane in accordance with the fingerprint pattern of said finger;
   (c) photodetector means having a light sensitive area for measuring the distribution of light impinging on said area;
   (d) optical means focused on said plane for transmitting said focused light pattern to said light sensitive area of said photodetector means; and
   (e) output means associated with said photodetector means for deriving said electric output signal in response to the pattern of light falling on said light sensitive area.

2. The fingerprint sensor according to claim 1, wherein said optical means comprises at least one imaging lens for imaging said focused light pattern to said light sensitive area of said photodetector means, said at least one imaging lens having an optical axis.

3. The fingerprint sensor according to claim 2, wherein said light sensitive area is tilted with respect to said optical axis, whereby said image of said focusing plane is in sharp focus on said light sensitive area.

4. The fingerprint sensor according to claim 1, wherein said contact surface is formed by a contact body having a light receiving surface on one side and said contact surface on the other.

5. The fingerprint sensor according to claim 4, wherein said light source passes light in forward direction obliquely through said light receiving surface to said contact surface.

6. The fingerprint sensor according to claim 5, further comprising a light stop for preventing undesired light reflected from said light receiving surface from passing to said light sensitive area.

7. The fingerprint sensor according to claim 1, wherein said light receiving surface and said contact surface are planar surfaces positioned at a small acute angle with respect to each other, wherein said optical means create an image of said light source in a plane between said contact body and said photodetector means, and wherein said light stop is arranged in said plane so as to capture said image of said source and to let substantially pass said reflected light beam from said contact surface.

8. The fingerprint sensor according to claim 7, wherein said acute angle is smaller than 5°.

9. The fingerprint sensor according to claim 8, wherein said wedge angle is smaller than 3°.

10. The fingerprint sensor according to claim 7, wherein said light stop has a sharp knife like edge.

11. The fingerprint sensor according to claim 4, wherein said contact body comprises a sensor plate made of elastic material and a light-transparent support plate attached to said sensor plate, said support plate forming said light receiving surface.

12. The fingerprint sensor according to claim 11, wherein said sensor plate is a plate having two parallel face ends, and wherein said support plate is a plate having a small acute angle between two face ends.

13. The fingerprint sensor according to claim 11, wherein said support plate is a glass plate.

14. The fingerprint sensor according to claim 11, wherein an optical matching medium is arranged between said sensor plate and said support plate, said optical matching medium contacting said sensor plate and said support plate.

15. The fingerprint sensor according to claim 4, wherein said contact body comprises a sensor plate made of elastic material, said sensor plate having a small acute angle between two face ends, one of said face ends being said light receiving surface and the other one of said face ends being said contact surface.

16. The fingerprint sensor according to claim 4, wherein said contact body comprises a sensor plate made of elastic material, said sensor plate having two parallel face ends, one of said face ends being said light receiving surface and the other one of said face ends being said contact surface.

17. The fingerprint sensor according to claim 4, wherein further optical means are arranged for passing said light from said light source to said light receiving surface, and wherein said further optical means comprises a collimator lens.

* * * * *